United States Patent [19]
DePonte

[11] Patent Number: 5,291,181
[45] Date of Patent: Mar. 1, 1994

[54] WET BED ALARM AND TEMPERATURE MONITORING SYSTEM

[76] Inventor: Dominic A. DePonte, 8822 Hornaday Cir., South #413, Fort Worth, Tex. 76112

[21] Appl. No.: 860,324

[22] Filed: Mar. 30, 1992

[51] Int. Cl.⁵ .............................................. G08B 21/00
[52] U.S. Cl. ................................... 340/604; 340/573; 128/886; 128/736; 604/361
[58] Field of Search ............... 340/603, 604, 605, 573; 200/61.04, 61.05; 128/886, 736; 604/361; 374/183, 208

[56] References Cited

U.S. PATENT DOCUMENTS

| | | | |
|---|---|---|---|
| 2,644,050 | 6/1953 | Seiger | 200/61.05 |
| 2,726,294 | 12/1955 | Kroening et al. | 200/61.05 |
| 2,866,454 | 12/1958 | McKenzie | 128/886 |
| 2,907,841 | 10/1959 | Campbell | 200/61.05 |
| 3,971,371 | 7/1976 | Bloom | 128/886 |
| 4,163,449 | 8/1979 | Regal | 128/886 |
| 4,271,406 | 6/1981 | Wilson | 340/604 |
| 4,356,479 | 10/1982 | Wilson | 340/604 |
| 4,800,370 | 1/1989 | Vetecnik | 340/573 |
| 5,036,859 | 8/1991 | Brown | 128/886 X |
| 5,074,317 | 12/1991 | Bondell et al. | 128/886 |

OTHER PUBLICATIONS

Article regarding use of Wet Stop by Palco Labs of Santa Cruz, Calif. (no date).

Primary Examiner—Jeffrey Hofsass
Attorney, Agent, or Firm—Oltman and Flynn

[57] ABSTRACT

An monitoring system for detecting urine includes an electric circuit for activating an indicator, having a break in continuity bordered by a pair of electrodes, a lead member extending from each electrode, the lead members being in a spaced apart relationship from each other, and a sheet of hydrophilic material extending over and resting against the lead members for absorbing and retaining urine to permit the urine to provide a conductive path between the lead members to complete the circuit and activate the indicator. The indicator is either a light or a sound generator. The system may additionally include a flexible sheet of waterproof material to which the lead members are joined. The flexible sheet of waterproof material optionally fits into a pocket of a bed pad. The system may additionally include a heat sensor for monitoring the temperature of a person resting against the sheet of hydrophilic material. Two independent and spaced apart heat sensors are optionally provided and measure the temperature differential at two different points on the flexible sheet to indicate by the magnitude of the differential whether the sheet is wet. The system also preferably includes a water-permeable cover sheet which extends across a side of the sheet of hydrophilic material opposite the lead members. Several of these systems may be independently monitored at a single annunciator panel.

12 Claims, 4 Drawing Sheets

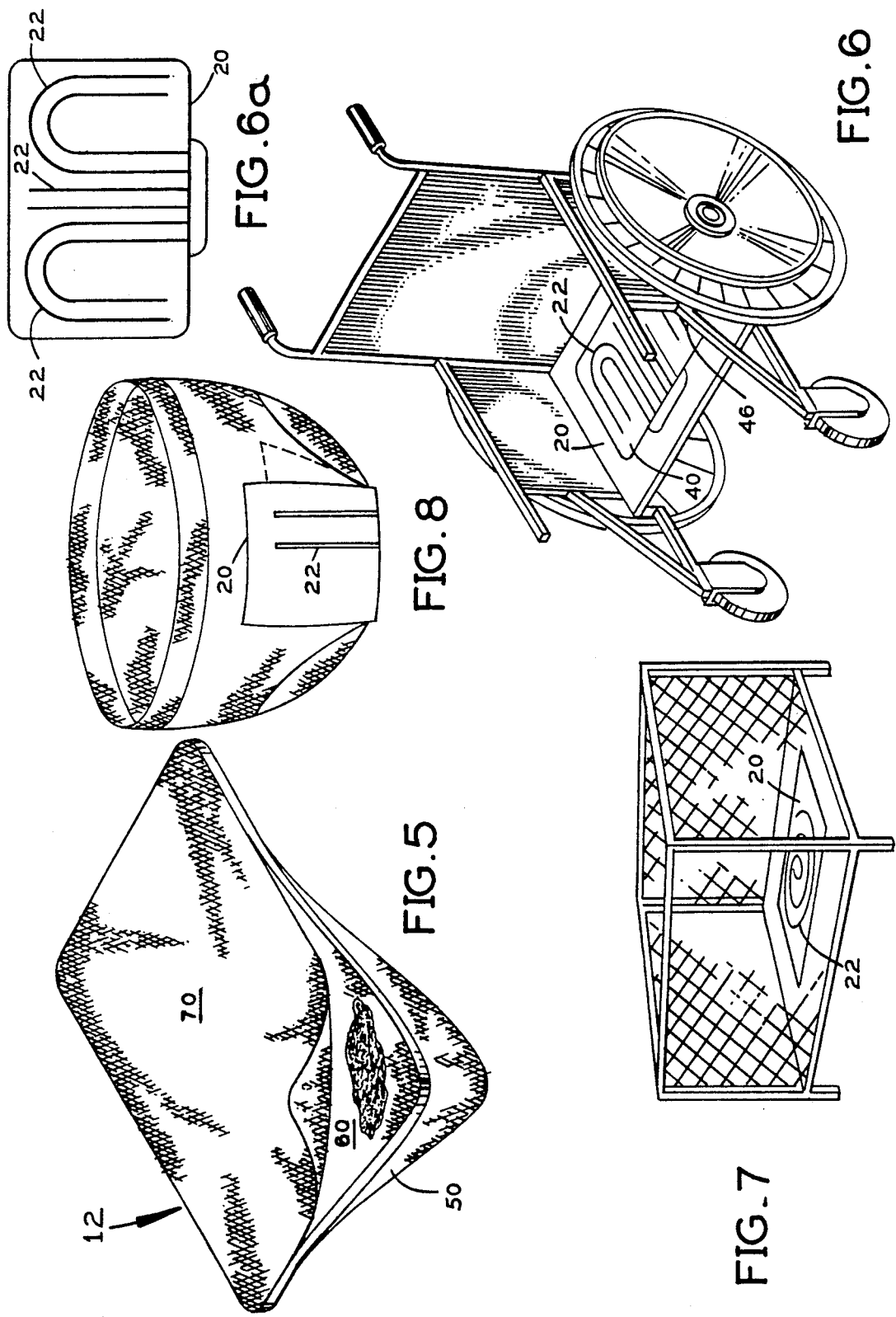

WET BED ALARM AND TEMPERATURE MONITORING SYSTEM

BACKGROUND OF THE INVENTION

1. Field of the Invention

The present invention relates generally to the field of systems for detecting liquids on beds, and more specifically to a urine detecting sensor pad including a waterproof substrate material having on its upper surface a pair of spaced apart and parallel strips of metallic ink material, each strip connected to a terminal of an alarm circuit, the sensor pad being inserted into a bed pad which has a bottom layer of waterproof material embossed on cloth, an absorbent middle layer which would lie on top of the inserted sensor pad, and a cloth top layer, such that urine deposited on the bed passes through the top layer and soaks the middle layer, providing both the liquid medium and electrolytes necessary to conduct a small electric current between the metallic ink strips and activate the alarm, and optionally including heat sensors to indicate fever or death by monitoring the temperature of a patient in the bed with a single sensor, and/or to indicate wetness or the presence of a high level of moisture by monitoring the temperature differential between two spaced apart sensors.

2. Description of the Prior Art

There have long been wet bed monitoring systems for sounding an alarm when a person urinates on a bed. These systems may sound the alarm when urine is present, but are often so sensitive that they sound false alarms when exposed to even a minute volume of virtually any liquid. They also tend to be difficult and expensive to manufacture and highly labor intensive to routinely clean.

The Prior art is aimed mainly at enuresis and incontinency problems. The present invention targets instant early detection systems for a health maintenance system that caters to persons suffering from pressure sore problems whose skin condition becomes very sensitive to and aggravated by the acetic urine liquid for long term patients in nursing homes, hospitals and at home. It is further intended as an aid to those patients who are heavily sedated or groggy from daily sedation who are incapable of requesting assistance in situations where early care is mandated.

Examples of such a prior art system include those of Wilson, U.S. Pat. No. 4,356,479, issued on Oct. 26, 1982, and Wilson U.S. Pat. No. 4,271,406, issued on Jun. 2, 1981. Both Wilson devices feature electrodes fabricated from permanent magnets which are held apart by a thin spacer. These magnets are attached to a patient's clothing or bed sheet. Urine completes the circuit between the electrodes to sound an alarm. A problem with Wilson is that the extent of the monitored area when a magnet is attached to a bed sheet is limited to the dimensions of the magnet, and if a patient happens to roll away from that spot and urinates elsewhere, the condition goes undetected. There is also some risk of danger from electric shock where the preferred embodiment including alternating current and the fuse system is employed. Finally, patient mobility is restricted where the option of attachment to the patient's garment is used, because the apparatus must be removed each time the patient gets out of bed.

Regal, U.S. Pat. No. 4,163,449, issued on Aug. 7, 1979, teaches a device which provides an aversive stimulus to a child who bed wets while asleep. Regal includes a urine detection pad of absorbent material having wire screen electrodes on either side of the pad which trigger an alarm when even a small amount of urine is present. A problem with Regal is that the sensor pad would react to any liquid, such as pure water, if soaking causes the wire screens to engage each other. Another problem with Regal is that it is designed to condition a child with an unpleasant sound rather than to alert a nurse or other health care worker at a distance.

Bloom, U.S. Pat. No. 3,971,371, issued on Jul. 27, 1976, discloses a urine sensing pad including a sheet of flexible insulating material carrying an array of conductive sensor strips on both of its faces. Moisture makes the electrical connection between the sensor strips to activate an alarm. A problem with Bloom is that the sensor strips are formed of aluminum tape and fastened to a Mylar pad with staples, which is a fragile construction. Cleaning such an arrangement is difficult, because urine seeps between the pick-up strips and sensor strips. Bacteria can be secluded among the layers, causing potential health problems. Another problem with Bloom is its complicated construction.

Campbell, U.S. Pat. No. 2,907,841, issued on Oct. 6, 1959, discloses a flexible support of dielectric material having crosswise electrodes traversing the width of the support. Alternate crosswise electrodes are attached to the different terminals of the circuit and the circuit is completed when an electrolyte shorts these electrodes, activating an alarm. A problem with Campbell is that free flowing urine is used to activate the device, so that the user must lye in this unabsorbed wetness until help arrives. Campbell is also cumbersome to build, uncomfortable to sleep on because nothing cushions contact with the electrodes and support, and it is difficult to clean. The metal foil is vulnerable to damage from rough handling.

McKenzie, U.S. Pat. No. 2,866,454, issued on Dec. 30, 1958, teaches metal grids of bronze wire; a plastic sheet and a pad to deliver shock treatment to a patient. A problem with McKenzie, apart from its design to shock rather than merely signal, is that it is clumsy and of intricate construction. Low reliability and high manufacturing costs are likely.

Seiger, U.S. Pat. No. 2,644,050, issued on Jun. 30, 1953, discloses a flat, thin, waterproof electro-insulative pad having embedded in its top face several thin metal conductors forming separated electrodes. The presence of urine shorts the electrodes and activates a signal. A problem with Seiger is that moisture is retained against the patient's skin while the signal is triggered. Another problem is that the caustic urine would quickly corrode the rubber and tin materials. Still another problem is that urine would seep into all the many crevices and make cleaning difficult and time consuming.

Kroening, U.S. Pat. No. 2,726,294, issued on Dec. 6, 1955, teaches two elongated flat thin plates of cardboard material, having metallic coatings on either side of the material. A problem with Kroening is that it would be difficult to clean urine from this multi-layer construction. Single use followed by disposal, on the other hand, would make Kroening prohibitively expensive to use. Another problem is that it is cumbersome to build and uncomfortable to sleep on.

It is thus an object of the present invention to provide a moisture monitoring system which is activated only by urine and a limited number of other liquids.

It is another object of the present invention to provide such a monitoring system which is comfortable and which draws urine away from the user to minimize irritating contact with the skin.

It is a further object of the present invention to provide a temperature monitoring system with a single heat sensor which is activated by a fever level temperature of a patient or by a temperature level which indicates patient discomfort.

It is a further object of the present invention to provide a temperature monitoring system, optionally incorporating two heat sensors, which measures the temperature differential between the two heat sensors to detect wetness or a high degree of moisture.

It is still another object of the present invention to provide such a monitoring system which is durable and easily cleaned for reuse.

It is finally an object of the present invention to provide such a monitoring system which is comparatively simple in design and inexpensive to manufacture.

SUMMARY OF THE INVENTION

The present invention accomplishes the above-stated objectives, as well as others, as may be determined by a fair reading and interpretation of the entire specification.

A monitoring system is provided for detecting urine, which includes an electric circuit for activating an indicator, having a break in continuity bordered by a pair of electrodes, a lead member extending from each electrode, the lead members being in a spaced apart relationship from each other, and a sheet of hydrophilic material extending over and resting against the lead members for absorbing and retaining urine to permit the urine to provide a conductive path between the lead members to complete the circuit and activate the indicator. The indicator preferably includes an indicator light. Alternatively, the indicator includes a sound generator. The system may additionally include a flexible sheet of waterproof material to which the lead members are joined. The flexible sheet of waterproof material optionally fits into a pocket of a bed pad. The system may additionally include a heat sensor for monitoring the temperature of a person resting against the sheet of hydrophilic material. The heat sensors are preferably of the washer variety, and are secured to the flexible sheet with buttons. The heat sensors are alternatively located on the bed sheet. Fasteners may be provided on the buttons to secure the flexible sheet to itself in a folded over configuration, such as hook and loop type fasteners. Two independent and spaced apart heat sensors are optionally provided and measure the temperature differential at two different points on the flexible sheet to indicate by the magnitude of the differential whether the sheet is wet. Alternatively, both sensors may be located on the bed sheet or one on the flexible sheet and the other on the bed sheet. The system also preferably includes a water-permeable cover sheet which extends across a side of the sheet of hydrophilic material opposite the lead members. Several of these systems may be independently monitored at a single annunciator panel, or a single remote transmitter and receiver unit.

BRIEF DESCRIPTION OF THE DRAWINGS

Various other objects, advantages, and features of the invention will become apparent to those skilled in the art from the following discussion taken in conjunction with the following drawings, in which:

FIG. 5 is a perspective, cut-away view of the bed pad, showing the three layers.

FIG. 6 is a representation of the system incorporated into a wheel chair, having three alarm circuits so that two serve as backups. The preferred circuit configuration is shown in FIG. 6a.

FIG. 7 is a representation of the system incorporated into a child's crib.

FIG. 8 is a representation of the system incorporated into a diaper for a child or an adult.

DETAILED DESCRIPTION OF THE PREFERRED EMBODIMENTS

Figure 1:
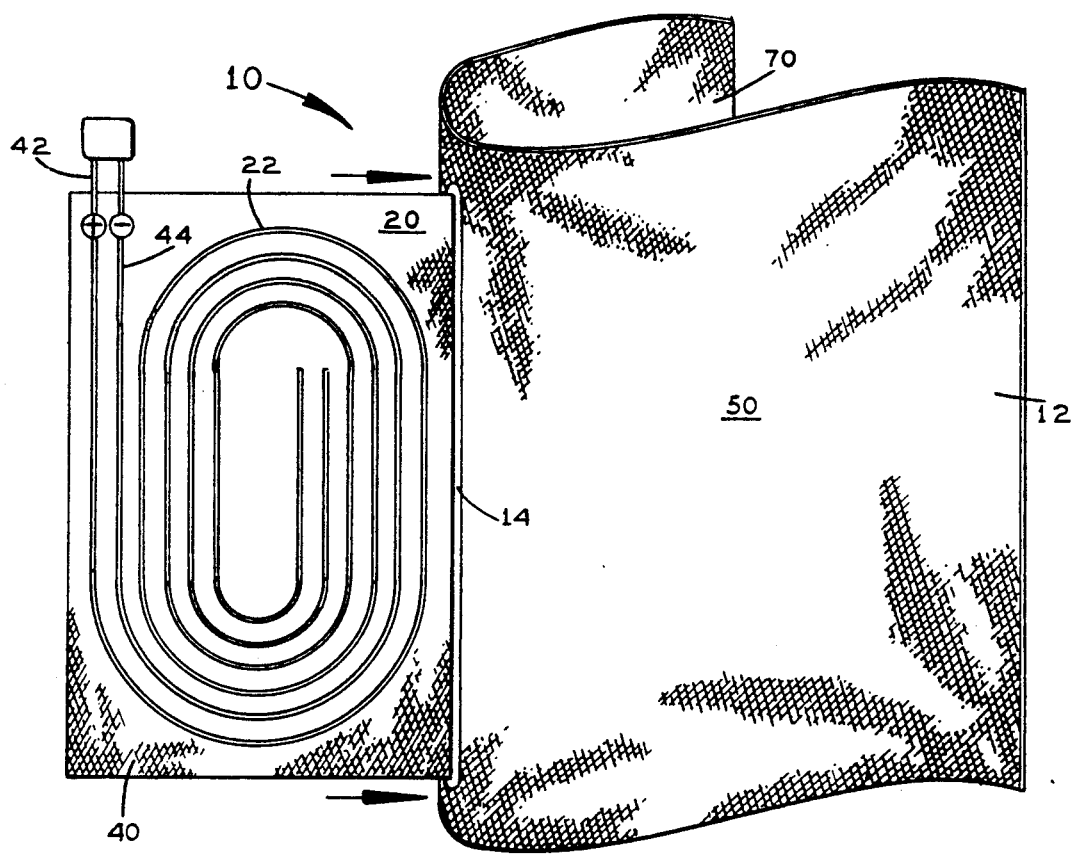
FIG. 1 is a bottom view of the bed pad showing the pocket and sensor pad of the preferred embodiment of the inventive monitoring system.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

FIRST PREFERRED EMBODIMENT

Referring to FIG. 1, a moisture monitoring system 10 is disclosed for use in hospitals, nursing homes and private homes. System 10 includes a bed pad 12 having a pocket 14 in its bottom surface into which is fitted a sensor pad 20 to which a pair of spaced apart electrode leads of an alarm circuit 22 are mounted. Alarm circuit 22 is completed and activated by the presence of a quantity of liquid containing an electrolyte which conducts current between the electrodes. Urine can activate the alarm because it contains an electrolyte.

Figure 2:
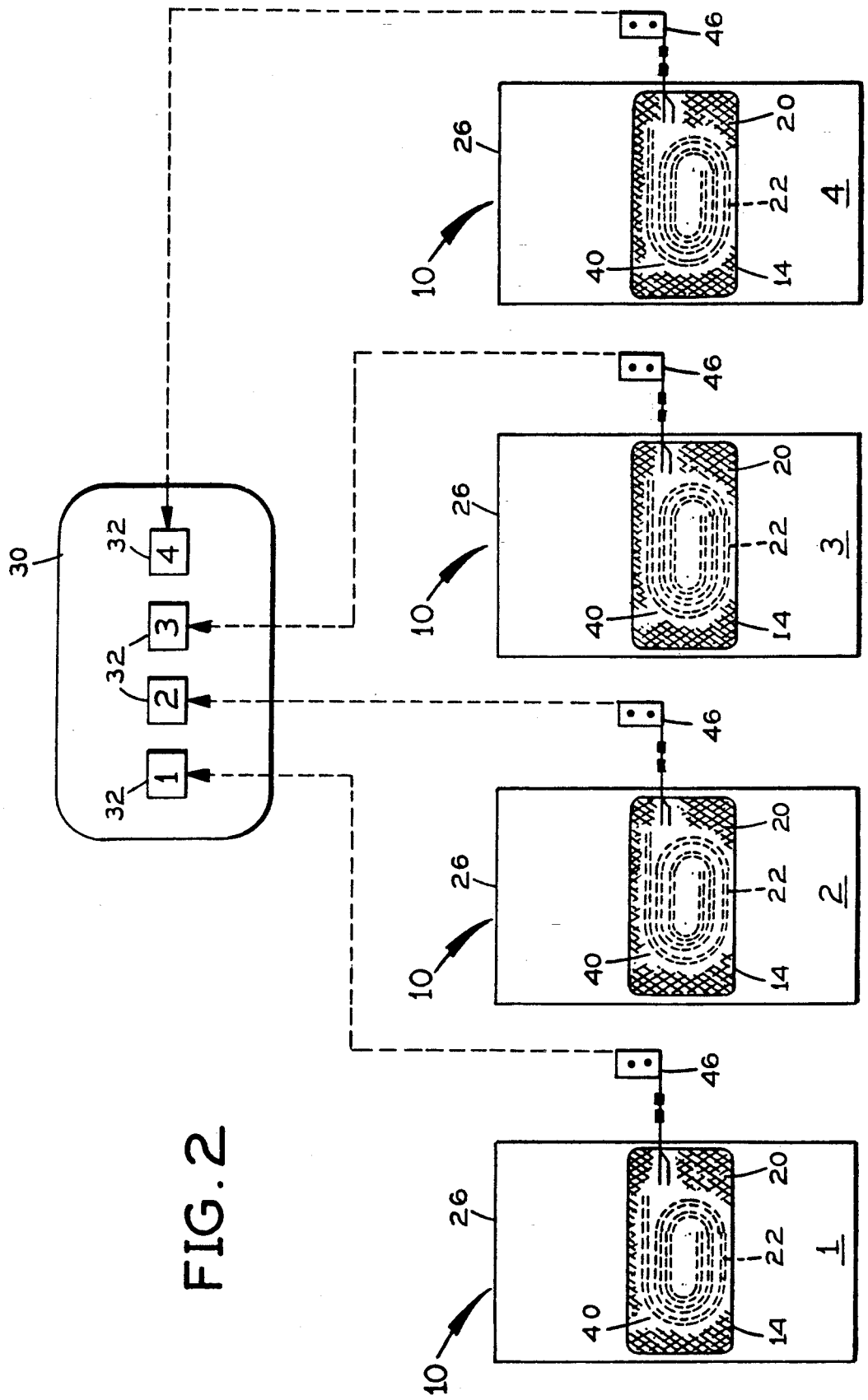
FIG. 2 is a schematic representation of several systems connected to an annunciator panel, separately monitoring four beds.

While a single alarm may be activated at the bed 26 itself, or on the doorway of the room where bed 26 is located, it is preferred that several beds 26 be so equipped and their circuits 22 all linked to a central monitoring board 30, such as at a nurses' station. See FIG. 2. Each circuit 22 is connected to a separate indicator 32 on board 30 so that the nurse at the station immediately knows when a bed 26 becomes wet and which bed 26 it is.

Figure 3:
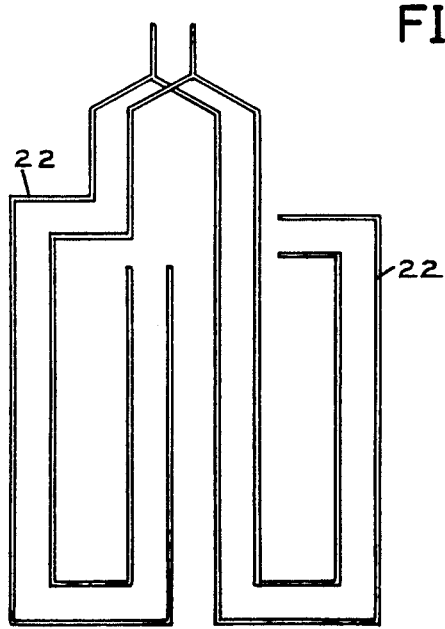
FIG. 3 is an optional circuitry pattern providing two separate and redundant circuits so that one backs up the other.
Figure 4:
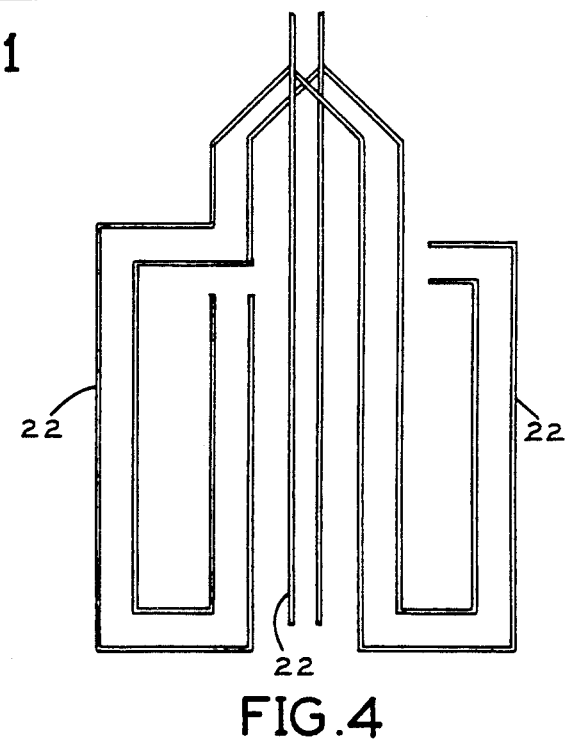
FIG. 4 is an optional circuitry pattern provided three separate and redundant circuits so that two back up the each one.

Sensor pad 20 preferably includes a waterproof substrate sheet 40 onto which two parallel conductive strips 42 and 44 of metallic ink material are preferably silk-screened, but can also be laminated, vulcanized or glued. The preferred waterproof material is polypropylene and/or elastagen, and the preferred metallic materials incorporate the use of silver ink, aluminum ink or graphite ink. Strip 42 is connected to a positive electrode and strip 44 is connected to negative electrode of circuit 22. Strips 42 and 44 preferably loop around the perimeter of sheet 40 and spiral inward for maximum coverage of the upper surface of sheet 40. Patterns other than loops are also contemplated. Multiple circuits 22 are preferably provided on sheet 40 for redundancy so that a backup is operative if one circuit 22 fails. See FIGS. 3 and 4. Circuit 22 is powered by a 9 volt battery and connected to a remote transmitter 46. Transmitter 46 sends a wireless signal to board 30, which is a receiver annunciator panel, or to a single receiver unit. The indicator 32 activated may be a siren or bell alarm, or a colored light.

Bed pad 12 preferably includes three layers of material. See FIG. 5. These layers include a waterproof bottom layer 50, into which pocket 14 is cut. On top of layer 50 is an absorbent middle layer 60 of hydrophilic synthetic fiber filling or cotton batting approximately one quarter inch thick. Layer 60 absorbs and retains urine, so that it is both drawn away from the patient and can serve to conduct current to activate circuit 22. This is a key inventive feature of system 10 because a small quantity of moisture, such as from perspiration, would not soak layer 60 sufficiently to make an electrical connection between strips 42 and 44. Where layer 60 is one quarter inch thick, prototype testing has revealed that one half cup to one cup of urine is needed to activate the alarm, but this varies depending on the type of hydrophilic material used and layer 60 thickness. Since the volume of urine discharged by a human being is almost invariably in excess of one cup, reliability is maintained while false alarms are minimized or eliminated. No less important is that ordinary spilled water does not activate the circuit and cause a false alarm. Urine is necessary because it provides the electrolytes needed as charge carriers. In contrast, a thimble-full of virtually any liquid would activate many of the prior art wet bed alarm devices. Finally, layer 60 provides a cushion between the patient and the electrodes for increased comfort.

On top of middle layer 60 is an insulating top layer 70, preferably of nylon or cotton fiber, which passes but does not substantially absorb liquids. Layer 70 helps separate the skin of the patient from the soaked middle layer 60 to minimize exposure to moisture and resulting irritation. Layer 70 also provides a durable outer surface for bed pad 12 for an increased useful life.

In summary, when a person wets bed 26, the urine passes through top layer 70 and soaks middle layer 60. Bottom layer 50 prevents the urine from reaching the mattress. The urine conducts electric current from strip 44 to strip 42 and thereby completes alarm circuit 22. The battery pack is energized as a result and circuit 22 then activates wireless transmitter 46. Transmitter 46 emits an electromagnetic signal of radio wavelength to a receiver which activates an indicator 32 at board 30. Board 30 is preferably located and monitored at a nurses' station. This permits prompt action to be taken to remove and replace the patient's wet clothing and bed pad 12 or to respond to a fever temperature of a patient or to a high level of heat discomfort that has been signaled.

Sensor pad 20 is removed from pocket 14 in bed pad 12 and sponged clean with soap and water, and then with a germicide, for reuse. Bed pad 12 is cleaned through conventional machine laundering. Alternatively, sensor pad 20 may be permanently incorporated into bed pad 12. In the latter instance, the entire bed pad 12 is simply machine laundered.

Also contemplated is a single sensor alarm for an individual bed, or a light installed over an entry door of a patient's room. The latter has been found through prototype testing to require two 9 volt batteries. Circuit pad 20 and circuit 22 may also be incorporated with a smaller version or size of bed pad 12 into a wheel chair, a child's crib, a diaper or other garment. See FIGS. 6-8. The wheel chair incorporates three permanently enclosed circuits 22, with two serving as backups, because of rugged use. For wheel chair use it is preferred that the entire pad 12 be launderable.

Figure 9:
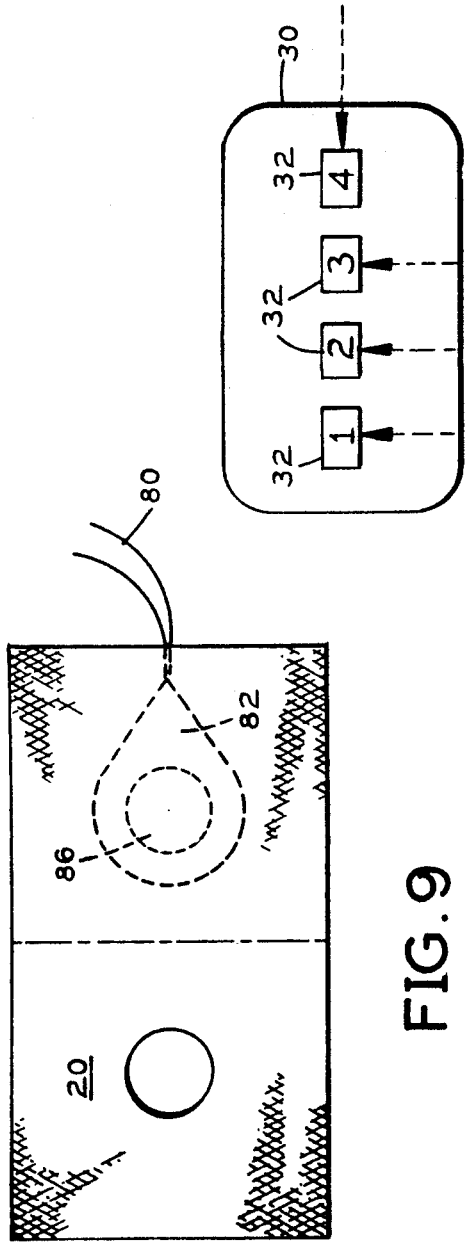
FIG. 9 is a schematic representation of a heat sensor and its mounting button.
Figure 10:
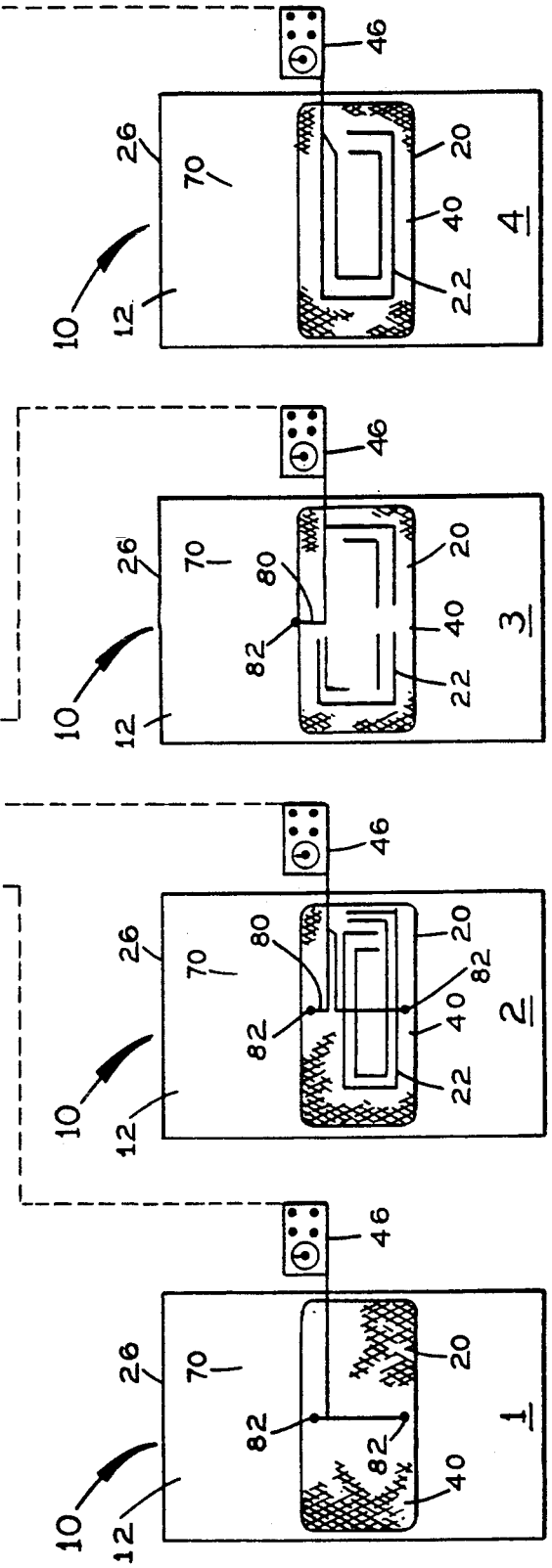
FIG. 10 is a schematic representation of multiple systems monitoring four beds, the first bed being equipped only with the two heat sensors, the second bed being equipped with two heat sensor tips and the moisture detecting circuit, the third with a single heat sensor to detect high temperature only and with the moisture detecting circuit, and the fourth bed being equipped with only the moisture detecting circuit.

An optional feature which may be included in sensor pad 20 is a single heat sensing circuit 80 to monitor the patient's temperature. A sufficiently high temperature would, of course, indicate a fever, while a very low temperature would indicate patient death. See FIG. 9. Optional dual heat sensors are provided to detect wetness or a high moisture level. See FIG. 10. Circuit 80 includes two separate and independent heat sensors 82 of the washer variety, preferably the SS washer thermocouple with teflon insulated leads and 20 gage elements produced by Nanmac, each mounted under a button 86. The top surface 88 of each button 86 is preferably covered with the hook or loop portion of a hook and loop fastener material such as VELCRO TM, so that pad 20 can be folded over itself and fastened. See FIG. 9. Each sensor 82 has a predetermined activating temperature, so that, for example, if the patient reaches 99 degrees F, the alarm will be activated. The preferred temperature monitoring device is the controlling mechanism produced by Nanmac, offering precise temperature control and alarms, which is currently used on engines of vehicles such as trucks.

Sensors 82 work in concert to achieve an additional purpose. The difference in temperature between sensors 82 is continuously measured. When one of sensors 82 is wet, its temperature is changed relative to the other sensor 82. When the differential exceeds a certain preprogrammed value, indicator 32 is activated, indicating a wet bed. In this way, heat sensors 82 serve to signal a fever temperature or the death of a patient, a high level of heat discomfort in bed, and also to provide a back up monitor for the wet bed circuit 22.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. A monitoring system for detecting urine and monitoring body temperature, comprising:

an electric circuit for activating indicator means, having a pair of electrodes having a break in continuity, a lead member extending from each said electrode, said lead members being in a spaced apart relationship from each other, a sheet of material extending over and resting against said lead members for absorbing and retaining urine to permit said urine to provide a conductive path between said lead members to complete said circuit and activate said indicator means, a flexible sheet of waterproof material to which said lead members are joined, heat sensor means for monitoring the temperature of a person resting against said sheet of material, said heat sensor means being of the washer variety, and being secured to said flexible sheet with button members, said heat sensor means comprising two independent and spaced apart heat sensors serving to also measure the temperature differential at two different points on said flexible sheet to indicate by the magnitude of said differential whether the sheet is wet.

2. A monitoring system according to claim 1, wherein the sheet of material is hydrophilic material.

3. A monitoring system according to claim 1, wherein the sheet of material is a bed sheet.

4. A monitoring system according to claim 1, wherein said indicator means comprise an indicator light.

5. A monitoring system according to claim 1, wherein said indicator means comprise sound generating means.

6. A monitoring system according to claim 1, wherein said flexible sheet of waterproof material fits into a pocket of a bed pad.

7. A monitoring system according to claim 1, wherein said heat sensors are secured to a bed sheet with button members.

8. A monitoring system according to claim 1, additionally comprising fastening means on said button members to secure said flexible sheet to itself in a folded over configuration.

9. A monitoring system according to claim 2, additionally comprising a water-permeable cover sheet which extends across a side of said sheet of hydrophilic material opposite said lead members.

10. An monitoring system according to claim 1, wherein multiple systems are independently monitored at a single annunciator panel.

11. A monitoring system for detecting urine and monitoring body temperature, comprising:

an electric circuit applied on an insulating substrate for activating indicator means, having a pair of electrodes having a break in continuity, a lead member extending from each said electrode, said lead members being in a spaced apart relationship from each other, a sheet of material extending over and resting against said lead members for absorbing and retaining urine to permit said urine to provide a conductive path between said lead members to complete said circuit and activate said indicator means, a flexible sheet of waterproof material to which said lead members are joined, heat sensor means for monitoring the temperature of a person resting against said sheet of material, said heat sensor means being of the washer variety, and being secured to said flexible sheet with button members, said heat sensor means comprising two independent and spaced apart heat sensors serving to measure the temperature differential at two different points on said flexible sheet to also indicate by the magnitude of said differential whether the sheet is wet.

12. A monitoring system according to claim 11 wherein said insulating substrate with said electric circuit thereon is sewn into a bed pad and made an integral part thereof.

* * * * *